United States Patent
Wortelboer et al.

(10) Patent No.: US 10,806,475 B2
(45) Date of Patent: Oct. 20, 2020

(54) TONGUE MANIPULATION DEVICE, BONE ANCHOR FOR USE IN SUCH DEVICE, CONTROL DEVICE AND AN ADJUSTMENT METHOD

(71) Applicant: KONINKLIJKE PHILIPS N.V., Eindhoven (NL)

(72) Inventors: Pippinus Maarten Robertus Wortelboer, Eindhoven (NL); Joachim Kahlert, Aachen (DE); Andrew East, Wilmington, MA (US); Bernd Engelbrecht, Landgraaf (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 658 days.

(21) Appl. No.: 15/109,456

(22) PCT Filed: Dec. 24, 2014

(86) PCT No.: PCT/EP2014/079296
§ 371 (c)(1),
(2) Date: Jul. 1, 2016

(87) PCT Pub. No.: WO2015/104190
PCT Pub. Date: Jul. 16, 2015

(65) Prior Publication Data
US 2016/0331390 A1    Nov. 17, 2016

Related U.S. Application Data

(60) Provisional application No. 61/925,716, filed on Jan. 10, 2014, provisional application No. 61/929,190, filed on Jan. 20, 2014.

(30) Foreign Application Priority Data

Jun. 3, 2014    (EP) .................................. 14170993

(51) Int. Cl.
*A61B 17/24*    (2006.01)
*A61F 5/56*    (2006.01)
(Continued)

(52) U.S. Cl.
CPC .......... *A61B 17/24* (2013.01); *A61B 17/0401* (2013.01); *A61B 17/7014* (2013.01);
(Continued)

(58) Field of Classification Search
CPC .......... A01K 89/0108; A01K 89/01081; A01K 89/01082; A01K 89/01085;
(Continued)

(56) References Cited

U.S. PATENT DOCUMENTS

2008/0023012 A1    1/2008    Dineen et al.
2008/0027560 A1    1/2008    Dineen et al.
(Continued)

FOREIGN PATENT DOCUMENTS

CN    202288400 U    7/2012
WO    2010138593 A1    12/2010
(Continued)

*Primary Examiner* — Tan-Uyen T Ho
*Assistant Examiner* — Chima U Igboko (57) ABSTRACT

A tongue manipulation device (10) has a tissue anchor (20) for attachment to the tongue, a bone anchor (22) typically for attachment to the mandible and a tether line (24) which fixes the tissue anchor to the bone anchor. The bone anchor comprises a tether line spool arrangement which comprises a spool (46) rotatable about a spooling axis and a spooling locking arrangement (54). The spooling locking arrangement is controlled by rotation about the spooling axis between spooling locking and permitting configurations. In this way, the physician implanting and setting the device can perform titration and subsequent locking as two independent operations.

14 Claims, 7 Drawing Sheets

(51) Int. Cl.
*A61B 17/70* (2006.01)
*A61B 17/04* (2006.01)
*A61B 17/00* (2006.01)

(52) U.S. Cl.
CPC .... *A61F 5/566* (2013.01); *A61B 2017/00814* (2013.01); *A61B 2017/0464* (2013.01); *A61B 2017/0496* (2013.01); *A61B 2017/248* (2013.01)

(58) Field of Classification Search
CPC ........ A01K 89/01086; A01K 89/01087; A01K 89/01088; A01K 89/0114; A01K 89/01141; A01K 89/01142; A01K 89/01143; A01K 89/0117; A01K 89/01931; A01K 89/0111; A01K 89/0113; A61B 17/7014; A61B 2017/0496; A61B 17/24; A61B 17/0401; A61B 2017/248; A61B 2017/00814; A61B 2017/0464; A61F 5/566

See application file for complete search history.

(56) References Cited

U.S. PATENT DOCUMENTS

| | | |
|---|---|---|
| 2009/0275954 A1 | 11/2009 | Phan et al. |
| 2011/0174852 A1 | 7/2011 | Young et al. |
| 2011/0282361 A1 | 11/2011 | Cabiri et al. |
| 2012/0266895 A1* | 10/2012 | Frazier ............... A61B 17/0401 128/848 |
| 2013/0197575 A1 | 8/2013 | Karapetian et al. |

FOREIGN PATENT DOCUMENTS

| | | |
|---|---|---|
| WO | 2013118069 A2 | 8/2013 |
| WO | 2014045165 A1 | 3/2014 |

* cited by examiner

TONGUE MANIPULATION DEVICE, BONE ANCHOR FOR USE IN SUCH DEVICE, CONTROL DEVICE AND AN ADJUSTMENT METHOD

CROSS-REFERENCE TO PRIOR APPLICATIONS

This application is the U.S. National Phase application under 35 U.S.C. § 371 of International Application Serial No. PCT/EP2014/079296, filed on Dec. 24, 2014, which claims the benefit of U.S. Application Ser. Nos. 61/925,716, filed on Jan. 10, 2014 and 61/929,190, filed on Jan. 20, 2014 and European Application Serial No. 14170993.1, filed Jun. 3, 2014. These applications are hereby incorporated by reference herein.

FIELD OF THE INVENTION

This invention relates to a tongue manipulation device, and particularly to the design of the bone anchor used in such devices. It also relates to a method of adjusting such devices as well as a control device (tool) for such adjustment.

BACKGROUND OF THE INVENTION

It is known to use a tongue manipulation device to treat upper airway obstruction and sleep disordered breathing.

Respiratory disorders during sleep are recognized as a common problem with significant clinical consequences. Obstructive Sleep Apnoea (OSA) causes an intermittent cessation of airflow. When these obstructive episodes occur, an affected person will transiently arouse. Because these arousal episodes typically occur 10 to 60 times per night, sleep fragmentation occurs which produces excessive daytime sleepiness. Some patients with OSA experience over 100 transient arousal episodes per hour. OSA may also lead to cardiovascular and pulmonary disease.

Various approaches are known which aim to maintain the airway passage during sleep. Oral appliances aimed at changing the position of the soft palate, jaw or tongue are available, but patient discomfort has limited their use. Continuous Positive Airway Pressure (CPAP) devices are often used as first-line treatments for OSA. These devices use a sealed mask which produces airflow at a slightly elevated pressure and acts to maintain positive air pressure within the airway.

This invention relates to an approach by which a tongue manipulation device is surgically applied to a patient. Aspire Medical was the originator of the "Advance" implantable tongue suspension technology.

Figure 1:
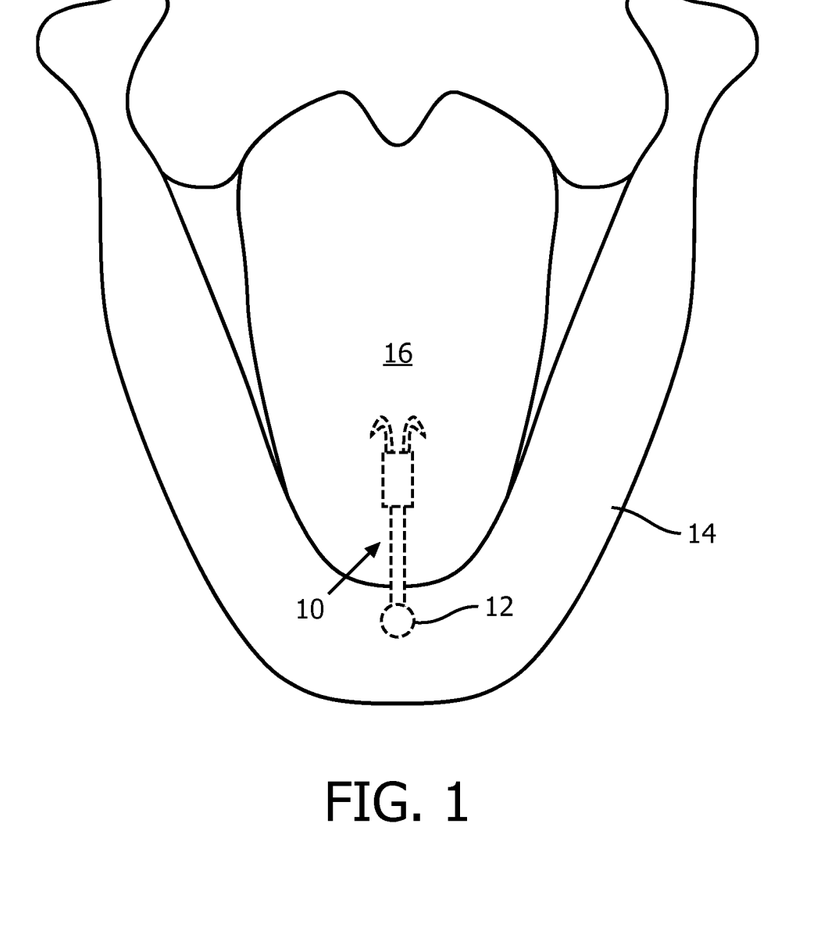
FIG. 1 shows generally how a known tongue manipulation device is used.
Figure 2:
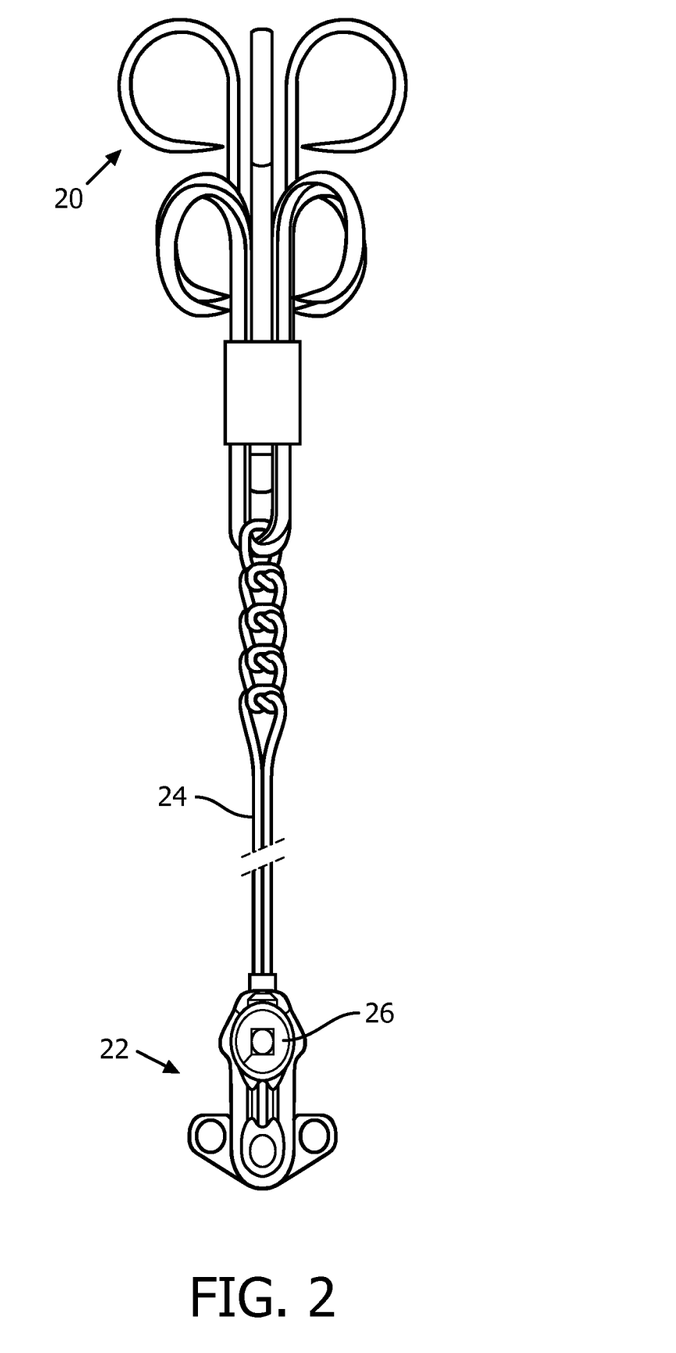
FIG. 2 shows the known tongue manipulation device in more detail.
Figure 3:
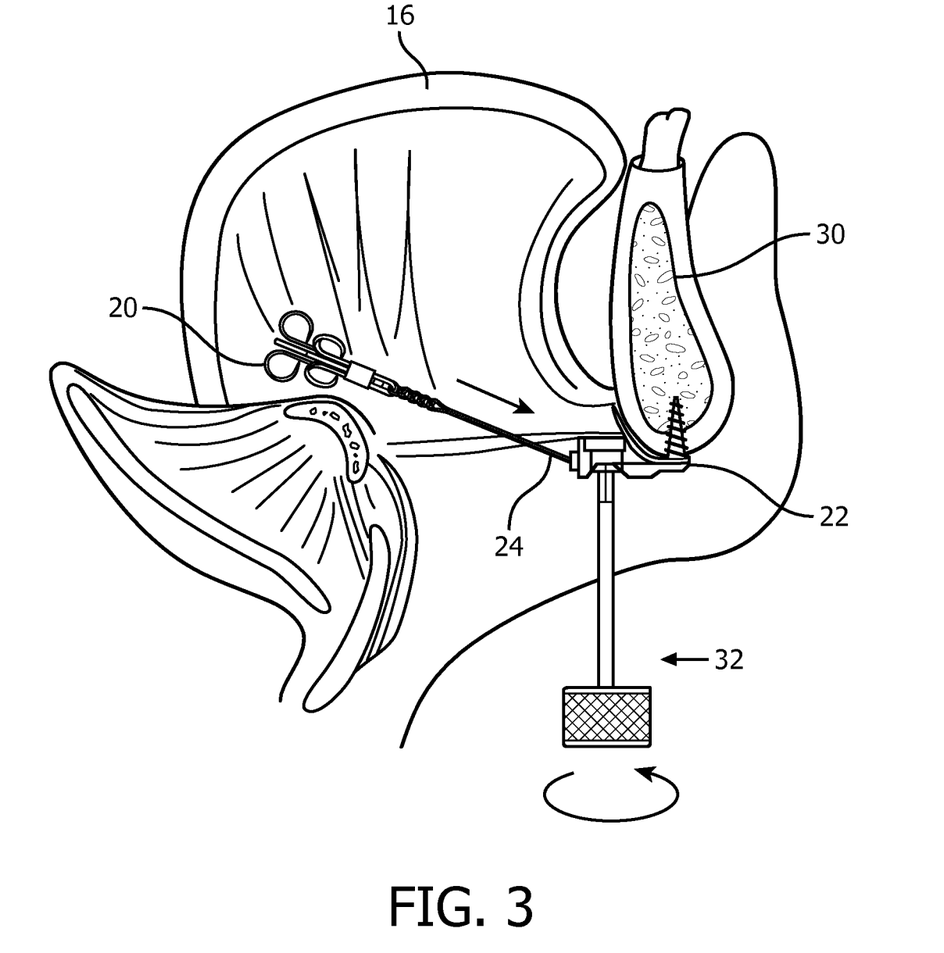
FIG. 3 shows how the tension in the tether line is adjusted in the device of FIGS. 1 and 2.

The technology is described in detail in US 2008/0023012 for example, on which FIGS. 1 to 3 are based.

The complete device comprises three essential parts:
(i) a tissue anchor which is surgically placed inside the tongue;
(ii) a bone anchor which is typically attached to the mandible; and
(iii) a tether line which fixes the tissue anchor to the bone anchor.

The bone anchor comprises a spool, enabling the surgeon to spool the tether into the bone anchor. This process is called titration and advances the tongue in the direction of the mandible (or prevents the tongue moving back), preventing blocking of the airway. The spool arrangement comprises an indexing part in the form of Nitinol click springs and a spool part, so that an audible sound is made during titration so that the number of titration steps can be counted. The Nitinol springs are pressed away in each spool step. The indexing part also retains the spool in a fixed position after adjustment, although a separate lock can be used. The spool has a fixed number of stable positions over one spool revolution. Clockwise turning (for example) provides titration (i.e. spooling up) of the tether line, and counter clockwise turning provides unspooling. The optimal advancement can be found by spooling back and forth.

Clinical studies have shown that the "Advance" technology is able to significantly reduce the number of apnoeic events in moderate and severe apnoea patients.

The stress level that the Nitinol springs experience can be above the limit that can guarantee sustained super-elastic behaviour; permanent deformation is likely to occur. Furthermore, the mechanism can be vulnerable once implanted.

Thus, one possible issue with the known designs is that with the spool position held by the indexing mechanism (i.e. in the absence of a separate mechanical locking device) unspooling of the tether can arise over time, if the indexing part fails. The indexing part can for example have an indexer spring that forces the spool to take one of the stable positions (for example there may be six such positions). If the indexing part fails through reduced spring stiffness, the holding torque is lost, leading to unspooling of the tether. Each titration step loads the springs which step by step can degrade the holding function.

The volume constraint does not allow a solution with the desired holding force without any spring behaviour degradation. Also the stable positions will not be accurate if the springs experience any permanent deformation.

WO 2013/118069 discloses a bone anchor for a tongue manipulation device which has a spool arrangement with an indexing part and a spool part. In a first configuration the spool part is operable to spool the tether line without operation of the indexing part, and in a second configuration the spool part is operable to spool the tether line with operation of the indexing part. This means the spooling to take up slack in the tether line does not cause wear to the indexing springs, and it also means the user can feel when the slack has been taken up.

This arrangement makes use of a separate adjustment needle which is not part of the bone anchor itself, which is used to turn the spool either freely or in indexed steps by selecting the appropriate needle insertion depth. At the deepest level the adjustment needle engages in an indexer part that provides a resistive torque when going from one stable spool position to the next.

The invention aims to provide a more simple to operate device.

SUMMARY OF THE INVENTION

According to the invention, there is provided a device and method as claimed in the independent claims.

In one aspect, the invention provides a bone anchor for a tongue manipulation device which comprises a tissue anchor for attachment to the tongue, the bone anchor and a tether line which fixes the tissue anchor to the bone anchor, wherein the bone anchor comprises a tether line spool arrangement, wherein the spool arrangement comprises a spool rotatable about a spooling axis and a spooling locking arrangement, and wherein the spooling locking arrangement is controlled by rotation about the spooling axis between spooling locking and spooling permitting configurations.

This arrangement uses rotation to provide spooling as well as a spooling lock function. This provides an easy to use device, which does not require pushing against the patient to engage the locking function. It also enables the spooling and locking to be performed with one tool without the need to change tools.

The bone anchor preferably further comprises an indexing arrangement which includes at least one component which is rotatable with the spool between indexing positions. The indexing arrangement is preferred but is nevertheless optional, because the spooling locking arrangement can provide the desired control.

In a first arrangement, the indexing arrangement comprises a polygonal indexing ring and spring members which engage with opposite side faces of the polygonal indexing ring.

The spooling locking part can comprise a (further) polygonal locking feature which rotates with the spool, and a sliding lock member which is slidable between locking engagement with the polygonal locking feature and release from the polygonal locking feature. The spooling locking part thus relies on mechanical gripping of a locking feature, which can for example be in the form of a hexagonal nut.

The sliding lock member can comprise a pair of facing flanges which are slidable between positions over corresponding faces of the polygonal locking feature or away from those corresponding faces. A converter can be used for converting between rotational movement about the spooling axis and sliding movement of the sliding lock member. In one arrangement, the converter comprises a rotatable head with an eccentrically positioned projection, and the sliding lock member has a slot within which the projection is received thereby to convert rotational movement of the projection into linear movement of the sliding lock member. This provides a simple and compact way to convert from rotation to reciprocal sliding, which can then be used to clamp or free the locking feature.

This first arrangement thus basically uses a sliding lock over a nut which rotates with the spool. This nut and lock is separate to the indexing part.

In a second arrangement, the spool comprises a set of spaced pillars, and the indexing arrangement comprises a ring around the spaced pillars, comprising a set of at least one sprung retaining members, which are spring-biased radially inwardly into the spacing between the pillars.

The spooling locking arrangement can then comprise a blocking member, rotationally movable between a blocking position in which the radial outer movement of the at least one sprung retaining member is blocked, and a free position in which the at least one sprung retaining member can deflect outwardly in response to movement of the spool.

This second arrangement thus basically clamps the spring parts of the indexing part by blocking the movement they need to make to allow indexing.

In both examples, a control shaft opening can be provided extending along the spooling axis, for receiving a control shaft, wherein the spool arrangement has a first control opening aligned with the control shaft opening, and the spooling locking arrangement comprises a second control opening of a different size aligned with the control shaft opening. This enables a single dual-core control shaft to be used to control the spooling and locking The invention also provides a tongue manipulation system, comprising a bone anchor of the invention. The system can comprise at least one of: a tissue anchor for attachment to the tongue and a tether line which couples the tissue anchor to the bone anchor.

The invention also provides a titration control device for a tongue manipulation device, comprising:
a handle assembly and a needle assembly projecting from the handle assembly to a distal end in a spool axis direction, wherein the needle assembly comprises:
an inner control shaft which terminates at an inner drive head at the distal end of the needle assembly, the inner control shaft rotatable by a first handle portion of the handle assembly;
an outer control shaft which terminates at an outer drive head, the outer control shaft rotatable independently of the inner control shaft by a second handle portion of the handle assembly;

The outer control shaft may terminate at the outer drive head set back from the distal end of the inner control shaft. The titration control device may comprises an outer sleeve within which the outer control shaft and/or the inner control shaft can rotate. The outer sleeve may terminate set back from the distal end of the inner and/or outer control shaft.

The invention can use this control device as part of a titration control system, comprising:
a tongue manipulation system of the invention; and
the titration control device.

Finally, the invention also provides a method of adjusting a tongue manipulation device which comprises a tissue anchor for attachment to the tongue; a bone anchor and a tether line which fixes the tissue anchor to the bone anchor, the method using a rotary drive member which engages with the bone anchor, the rotary drive member having an output shaft of two concentric rotatable shafts, wherein the method comprises:
if required, rotating a first shaft of the rotary drive member to cause a spooling lock to be released;
rotating a second shaft of the rotary drive member to cause spooling of the tether line onto the bone anchor until slack in the tether line is removed and/or the tether line is properly tensioned for the tongue manipulation; and
rotating the first shaft of the rotary drive member to cause the spooling lock to be engaged.

BRIEF DESCRIPTION OF THE DRAWINGS

Examples of the invention will now be described in detail with reference to the accompanying drawings, in which:

Iin schematic form the concept of the tension adjusting arrangement of the invention for use in the device of FIGS. 1 to 3;

FIG. 4 shows a first example of tension adjusting arrangement of the invention for use in the device of FIGS. 1 to 3; and FIG. 5 shows a second example of tension adjusting arrangement of the invention for use in the device of FIGS. 1 to 3.

DETAILED DESCRIPTION OF THE EMBODIMENTS

The invention relates to tongue manipulation devices having a tissue anchor for attachment to the tongue, a bone anchor typically for attachment to the mandible and a tether line which fixes the tissue anchor to the bone anchor. The bone anchor comprises a tether line spool arrangement which comprises a spool rotatable about a spooling axis and a spooling locking arrangement. The spooling locking arrangement is controlled by rotation about the spooling axis between spooling locking and permitting configurations. In this way, a spooling lock function can be implemented by rotation, so that it does not require pushing against the patient.

The invention can be applied as a modification to known devices, for example of the type described in detail in US 2008/0023012, which is hereby incorporated by reference.

The relevant parts of the known device will first be described, with reference to FIGS. 1 to 3 which are adapted from US 2008/0023012.

FIG. 1 shows a tongue manipulation device 10 attached to a securing assembly 12 located on the inferior surface of the mandible 14. The tongue is shown as 16.

FIG. 2 shows a possible design of the tongue manipulation device in more detail.

It comprises a tissue anchor 20 for attachment (in particular implantation) to the tongue and a bone anchor 22 for attachment to the mandible. A tether line 24 fixes the tissue anchor to the bone anchor.

The bone anchor 22 comprises a tether line spool arrangement 26. This enables the tether line to be wound onto the spool to take up slack in the tether line so that the line can provide a desired restricted movement of the tongue.

FIG. 3 shows how adjustment of the spool is made, and shows a cross section through the lower part of the head of a patient. The bone anchor 22 is attached to the lower mandible 30 as shown. To tighten the tether line 24, a rotary drive shaft 32 (known as a "titration needle") is inserted into an opening in the spool part of the bone anchor, and adjustment is judged based on an indexed function.

The invention provides an arrangement in which two rotating parts are used, sharing the same rotation axis (so that a shared dual shaft control tool can be used). One is the tether line spool arrangement which preferably includes an indexing arrangement, and the other is a spooling locking arrangement for locking the spool (and thereby locking the indexing arrangement as well if provided).

Figure 4:
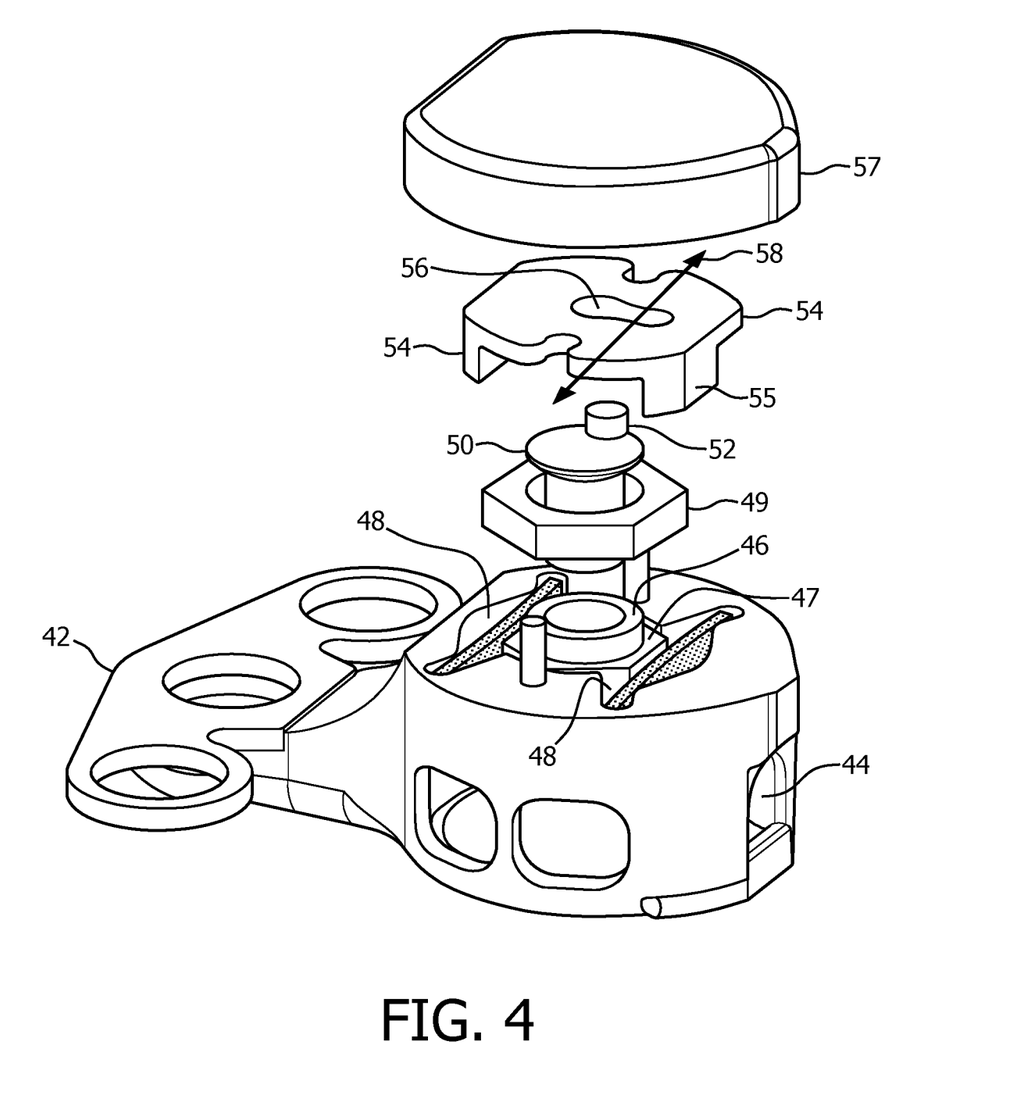
FIG. 4 shows a first example of bone anchor of the invention.

A first example is shown in FIG. 4, which shows the bone anchor 22 in an exploded view.

The bone anchor has a bone fixing 42 and a tether line port 44. A spool 46 is used for winding the tether line. The spool is fixed to a hexagonal indexer 47 which engages with Nitinol (or other) click springs 48. In the design shown, the indexer engages with a pair of click wires to provide six stable spool positions. A top of the spool has a spooling locking feature, 49 in the form of a hex nut ring. Note that this locking feature also functions an indexer (although it is part of the spooling locking arrangement), in that it defines set positions in which the spool can be held (as will be clear from the description below).

A converter 50 is rotated by as part of the locking function, and has an eccentric protrusion 52. This engages with a slider lock plate 54 which performs a locking function. The slider lock plate 54 has a pair of locking flanges 55 which extend over faces of the locking feature. The top surface of the slider lock plate 54 has an elongate slot 56 which receives the protrusion 52 when assembled. A cover plate 57 is at the top.

This design makes use of a slider lock.

The hexagonal locking feature 49 is fixed to the spool 46 and provides a pair of opposing edges to lock spool rotation. The slider lock plate 54 is constrained in its possible motion by engagement with the protrusion 52 and can only move back and forth in a direction 58 perpendicular to the spool axis.

The slot 56 is elongate, so that it converts the eccentric rotation of the protrusion 52 into linear motion in parallel to the direction 58. For this purpose the slot extends in a direction perpendicular to the direction 58 but in the same plane.

In a forward position of the slider lock plate 54, the flanges 55 do not contact the sides of the hexagonal locking feature 49 and the spool 46 is free to rotate.

In a back position of the slider lock plate 54, the flanges engage the edges of the hexagonal locking feature 49 and the spool is locked.

The slider lock plate 54 is driven by the converter 50 that has the same axis of rotation as the spool 46. The converter 50 is basically a cylindrical component with an eccentric cylindrical protrusion 52 at the top, and hollow at the bottom. The converter 50 can be turned from outside (from the bottom in FIG. 4) using a small needle part with a head that engages precisely in the slot of the hollow. Note that the converter 50 and the spool 46 are rotatable independently, by a tool described further below, so that the locking and unlocking functions are performed as one rotational operation, and the spooling or unspooling is performed as a separate rotational operation.

As the cylindrical shape on top is placed eccentrically, turning the converter by 180 degrees effectively moves the second cylinder to the opposite side while dragging the slider lock plate. The slot in the slider lock plate is elongate to allow the eccentric protrusion to move freely. The length of the slot will determine the amount of linear sliding that is possible, and corresponds to a range of angular rotation of the converter 50. Thus, the slot ends can act as stops which limit the possible rotation of the converter. For example, the converter can be limited to a rotation range of around 90 degrees. The width of the slot corresponds to the width of the protrusion.

In principle there is actually no need for the indexing arrangement 47,48 in this embodiment. The spool can be turned freely to a position where the spooling lock can be activated. When used, the indexing arrangement of the spool helps in stabilizing the six positions before the lock is shifted into place.

The indexing arrangement is preferably strong enough to keep its position for the expected loads on the tether line that are present when locking is desired.

Note that in this arrangement, the locking feature 49, the converter 50 and the slider lock plate can all be considered to be parts of a spooling locking arrangement (whether or not the separate indexing ring 47 is used).

Figure 5:
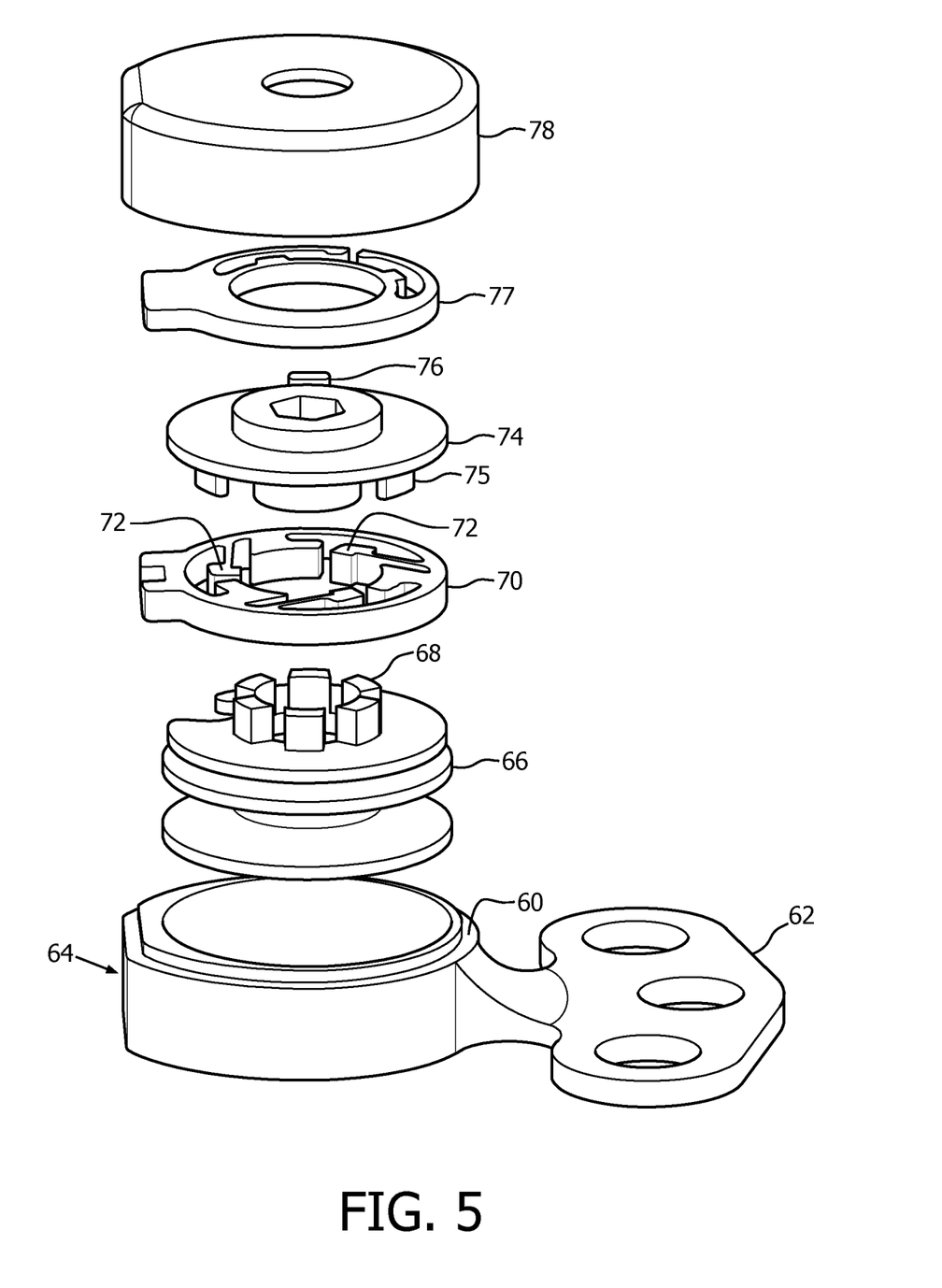
FIG. 5 shows a second example of bone anchor of the invention.

FIG. 5 shows a second example, which again shows the bone anchor 22 in an exploded view.

The bone anchor 22 comprises a base part 60 with a bone fixing 62 and a tether line port 64.

The top of the spool 66 has a six-pillar extension ring 68 on top. Above the spool is a click finger plate 70. This comprises a set of flexible elements in the form of click fingers 72, described and shown in more detail below. A rotation lock 74 is provided over the click finger plate 70. A lock stop plate 77 is provided over the rotation lock 74, and there is again a top cover 78. This rotation lock 74 thus again functions as a spooling locking arrangement, and it locks the spooling and indexing operations.

This arrangement functions by turning blocking bosses behind flexible elements (the click fingers 72) that need to flex out to allow the spool to rotate from one index position to the next.

For the purposes of this description, it is assumed that the number of index positions is n. To have n index positions, n axial grooves (or slits) are made on the spool 66 at a well defined fixed angle from each other ($2\pi/n$). These axial grooves are the spaces between the pillars of the extension ring 68.

The click finger plate 70 contains click fingers 72 that can only engage in the grooves between pillars when the spool is in one of the n positions. In this case, each of the click fingers engages with the grooves in the extension ring.

Note that the flexible click fingers can be attached either to the spool or to the click finger plate, so that the fingers and grooves can be interchanged compared to the example shown.

The number of click fingers should not exceed n. For maximum holding force to keep the spool in an indexed position it can be exactly n. It can be a fraction of n, and the example shown has 3 click fingers for a 6 position spool.

In other spool positions the click fingers are deflected. The click fingers 72 are designed such that this deflection is fully elastic.

In the indexed positions, the click fingers return (almost) to their natural shape. The torque needed to lift the finger tips out of the grooves can be optimized for instance by using formulas for straight or curved cantilever beam stiffness.

The basic idea of this embodiment is that the rotation lock 74 disables the indexer. One way to lock the fingers when they are in the indexed position is by shifting a boss behind the fingers. These bosses are mounted on the rotation lock 74 that can be rotated back and forth to lock and unlock the fingers.

Figure 6:
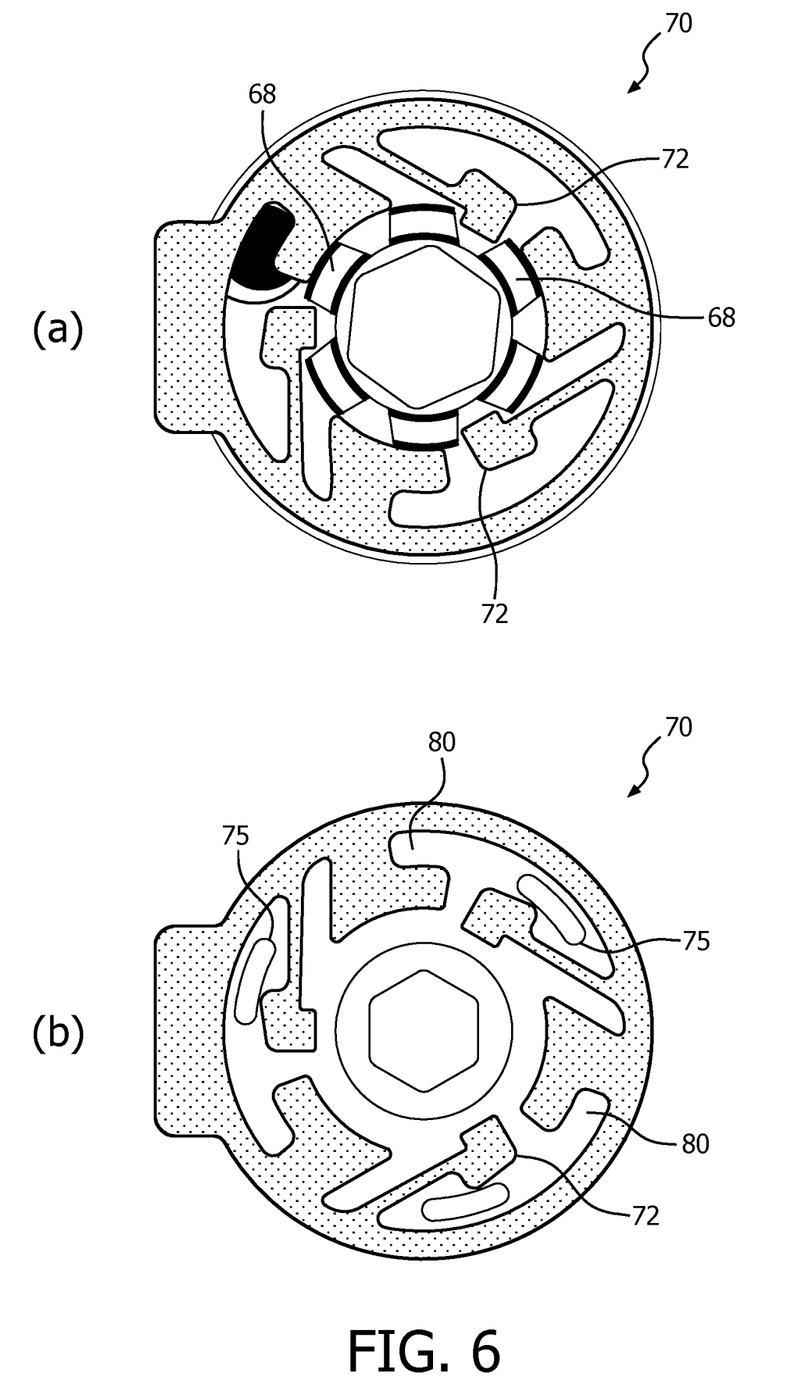
FIG. 6 shows the indexing and locking arrangement of the bone anchor of FIG. 5 in more detail.

FIG. 6(*a*) shows a top view of the click finger plate 70. There are three click fingers 72. The click fingers are shown engaging into the slots between the pillars 68.

The rotational lock has three bosses 75 at the bottom side to block the three click fingers and prevent them from flexing radially outwardly. It also has a boss 76 at the top side to engage in a slot of the lock stop plate 77. This controls the range of angular movement which is permitted for the rotation lock 74.

FIG. 6(*b*) shows the click finger plate from beneath, so that the bosses 75 of the rotation lock can be seen. These function as blocking members.

When applying a torque to the spool, the pillars 68 of the spool move the tips outward. The spool is driven by an Allen key like tool of a size fitting in the spool hole. However, this rotation is only possible when the locking bosses are in the disabled position and not when the locking bosses are right above the finger tips. This locked position is shown in FIG. 6(*b*).

By moving the lock plate over around 40 degrees counterclockwise the bosses will move into the disabled position 80 and the lock is made inactive. The Allen key to turn the lock plate 70 is smaller than the key to turn the spool.

As for the example above, the rotation lock 74 and the spool 66 are rotatable independently, by the tool described further below, so that the locking and unlocking functions are performed as one rotational operation, and the spooling or unspooling is performed as a separate rotational operation.

The design of the click finger plate 70 is not restricted to 3 click fingers or straight fingers. An alternative with three curved fingers can for example require less space.

In both examples, the spool and rotatably-driven locking feature (54 and 74) can be rotated using two separate dedicated tools with the right tool tip to fit firmly into the hole of concern. The tools can have a needle/shaft length and hand grip that allow operation at the required torque and ideally incorporate a torque limiter to avoid damage to the lock or adjustment mechanism.

Alternatively the two tools can also be integrated. In this way, a combined tool for titration and index locking is enabled. The advantages are that there is no longer a need to first withdraw a titration tool and insert an index locking locking tool to start locking after advancement has been finalized, and that spontaneous unspooling after advancement can be avoided by directly activating the lock while the adjustment tool part keeps the spool in place.

Figure 7:
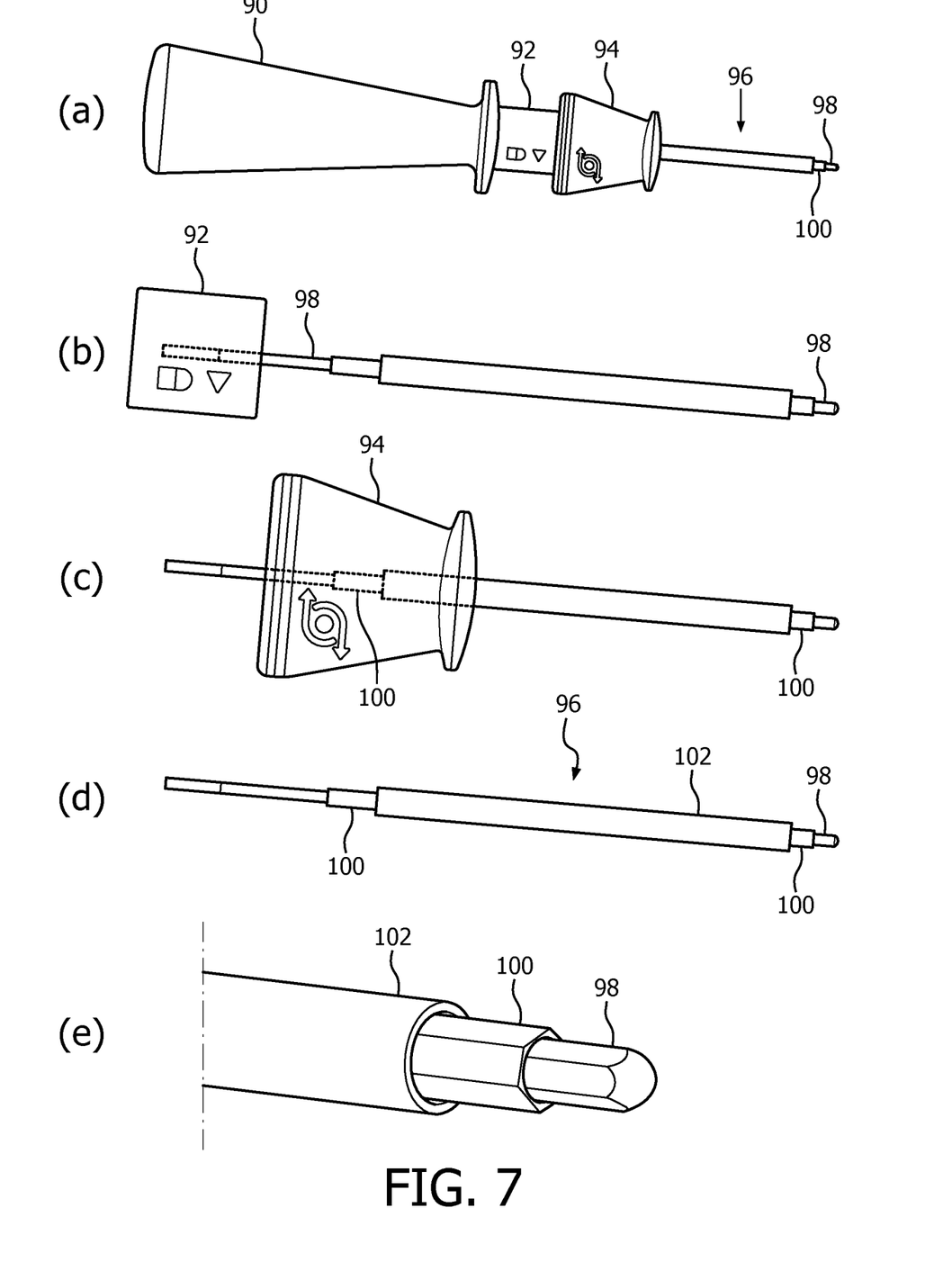
FIG. 7 shows a titration control device of the invention.

FIG. 7 shows one example of combined tool assembly for this purpose.

FIG. 7(*a*) shows the full tool assembly. It comprises a handle 90, a lock/unlock control section 92, an adjustment section 94 for controlling titration and an assembly of needles 96. This needle assembly 96 has at least two concentric parts, in the form of a smaller inner control shaft 98 which projects distally beyond the larger outer control shaft 100. They each terminate at a drive head.

The lock/unlock control section is shown in more detail in FIG. 7(*b*). It controls the rotation of the inner (longer) needle part. For example, a counter clockwise step is used for unlocking, and a clockwise step back is used for locking The lock knob 92 and lock/unlock central needle part 98 are rigidly connected.

The second, outer needle 100 is a control shaft that can be rotated independently. FIG. 7(*c*) shows the parts 94,100 involved in tether line adjustment (i.e. titration). The adjustment section is shown transparent to show that the inner hole of the adjustment knob and the outer diameter of the outer adjustment control shaft 100 connect to each other.

The components of the needle assembly 96 are shown in more detail in FIG. 7(*d*).

There is an outer sleeve 102 at the outside of the needle assembly 96 which can rotate freely over the outer control shaft 100. The outer sleeve which terminates set back from the distal end of the outer control shaft 100 and it can be fixed with respect to the adjustment section 94.

It serves two purposes. The first is that it remains in a fixed position in the channel of operation to avoid damage and irritation along the created access path in the human body while doing the adjustment. This can be achieved either by fixing the outer sleeve to the adjustment section 94 or by allowing it to rotated freely, in which case it will be held rotationally still by contact with the patient. The second is that its distal end provides a stop; the distance over which the inner lock control shaft 98 and outer control shaft 100 can be pushed into the corresponding bone anchor components is limited, thus protecting these components from damage due to excess of pushing force.

FIG. 7(*e*) shows the tip of the needle assembly 96 in more detail. In this example, both the lock/unlock control shaft 98 and the outer control shaft 100 have an outer hexagonal shape. Their sizes match the hole dimensions of the corresponding bone anchor components.

It can be seen from the two examples above that the invention provides a design with two rotating parts. The first can be the actual spool to wind tether, and the second can be the driver of a mechanism to block the spool. Both bodies can have the same axis of rotation, so that they have coaxial parts, and have non-circular holes for engagement with corresponding needle tips. The proximal one has a larger hole.

The tool head for this proximal body cannot penetrate into the distal hole. The smaller tool head for the distal body can rotate freely in the proximal body hole. The tool has coaxial shafts for engaging with the bone anchor.

In one embodiment, the deeper slot (of the distal body) can be reached only by the needle part which is for locking the spool. This needle part is then free to rotate in the higher slot (of the proximal body). The titration/adjustment needle part is bigger and matches the spool slot but cannot enter the lock slot. In principle the functions of locking and titration can also be interchanged so that the spooling/titration control is deeper in the device and the locking is shallower in the device.

The mechanism to put the blocking element(s) in place can be of different types, however in each type, it is driven by a pure rotation. One type blocks the spool itself and is applicable to all kind of spools. It can use an eccentric disc to convert a rotation into a translation of a slider that can engage in or over the spool when it is oriented correctly. To ensure the orientation is correct any indexing function can be added to the spool. Another type blocks the spool by preventing indexer elements to deflect when in one of the indexed positions. In this way, it does not directly block the spool, but blocks the transition from one indexed position to the other.

It will be clear that the invention resides in the spooling arrangement forming part of the fixed bone anchor part. The invention thus relates to the bone anchor part in isolation as well as to the tongue manipulation device as a whole.

In the examples shown, a hexagonal drive head is at the end of each control shaft of the tool. Of course, this can be any other interlocking shape, including a screwdriver type head for the inner control shaft, and other polygons or more complicated bolt head designs. The openings in the spool and rotatable index locking part will be designed to correspond.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A bone anchor assembly for use in a tongue manipulation device that comprises:
    a tissue anchor for attachment to the tongue,
    a bone anchor, and
    a tether line which fixes the tissue anchor to the bone anchor,
    wherein the bone anchor comprises a tether line spool arrangement,
    wherein the spool arrangement comprises a spool rotatable about a spooling axis and a spooling locking arrangement, and
    wherein the spooling locking arrangement is controlled solely by rotation about the spooling axis between a first positioning in which the spool is locked, and thus not rotatable about the spooling axis, and a second positioning in which the spool is unlocked and thus is rotatable about the spooling axis.

2. A bone anchor assembly as claimed in claim 1, further comprising an indexing arrangement which includes at least one component which is rotatable with the spool between indexing positions.

3. A bone anchor assembly as claimed in claim 2, wherein the indexing arrangement comprises a polygonal indexing ring and spring members which engage with opposite side faces of the polygonal indexing ring.

4. A bone anchor assembly as claimed in any preceding claim, wherein the spooling locking arrangement comprises a polygonal locking feature which rotates with the spool, and a sliding lock member which is slidable between locking engagement with the polygonal locking feature and release from the polygonal locking feature.

5. A bone anchor assembly as claimed in claim 4, wherein the sliding lock member comprises a pair of facing flanges which are slidable between positions over corresponding faces of the polygonal locking feature or away from those corresponding faces.

6. A bone anchor assembly as claimed in claim 4, wherein the spooling locking arrangement further comprising a converter for converting between rotational movement about the spooling axis and sliding movement of the sliding lock member.

7. A bone anchor assembly as claimed in claim 2, wherein the spool comprises a set of spaced pillars, and the indexing arrangement comprises a ring around the spaced pillars, comprising a set of at least one sprung retaining members, which are spring-biased radially inwardly into the spacing between the pillars.

8. A bone anchor assembly as claimed in claim 7, wherein the spooling locking arrangement comprises a blocking member, rotationally movable between a blocking position in which the radial outer movement of the at least one sprung retaining member is blocked, and a free position in which all sprung retaining members can deflect outwardly in response to movement of the spool.

9. A bone anchor assembly as claimed in any preceding claim, comprising a control shaft opening extending along the spooling axis, for receiving a control shaft, wherein the spool arrangement has a first control opening aligned with the control shaft opening, and the spooling locking arrangement comprises a second control opening of a different size aligned with the control shaft opening.

10. A tongue manipulation system, comprising a bone anchor assembly as claimed in claim 1.

11. A titration control device adapted to control a tongue manipulation system as claimed in claim 10, comprising:
    a handle assembly and a needle assembly projecting from the handle assembly to a distal end in a spool axis direction,
    wherein the needle assembly comprises:
        an inner control shaft which terminates at an inner drive head at the distal end of the needle assembly, the inner control shaft rotatable by a first handle portion of the handle assembly;
        an outer control shaft which terminates at an outer drive head, the outer control shaft rotatable independently of the inner control shaft by a second handle portion of the handle assembly, wherein one of the inner and outer drive heads is adapted to control rotation of the spool of the bone anchor and the other of the inner and outer drive heads is adapted to control rotation of the spooling locking arrangement of the bone anchor.

12. A titration control device as claimed in claim 11, wherein the outer control shaft terminates at the outer drive head set back from the distal end of the inner control shaft and/or wherein the titration control device further comprises an outer sleeve within which the outer control shaft can rotate.

13. A titration control system, comprising:
    a tongue manipulation system as claimed in claim 10.

14. A bone anchor assembly for use in a tongue manipulation device that comprises:
    a tissue anchor for attachment to the tongue;
    a bone anchor; and
    a tether line which fixes the tissue anchor to the bone anchor,
    wherein the bone anchor comprises a tether line spool arrangement,
    wherein the spool arrangement comprises a spool rotatable about a spooling axis and a spooling locking arrangement,
    wherein the spooling locking arrangement is controlled by rotation about the spooling axis between a first positioning in which the spool is locked, and thus not rotatable about the spooling axis, and a second positioning in which the spool is unlocked and thus is rotatable about the spooling axis,
    wherein the spooling locking arrangement comprises a polygonal locking feature which rotates with the spool, and a sliding lock member which is slidable between locking engagement with the polygonal locking feature and release from the polygonal locking feature,
    wherein the spooling locking arrangement further comprises a converter for converting between rotational movement about the spooling axis and sliding movement of the sliding lock member, and
    wherein the converter comprises a rotatable head with an eccentrically positioned projection, and the sliding lock member has a slot within which the projection is received thereby to convert rotational movement of the projection into linear movement of the sliding lock member.

\* \* \* \* \*